(12) United States Patent
Izumi et al.

(10) Patent No.: US 7,955,789 B2
(45) Date of Patent: Jun. 7, 2011

(54) ADHESION-PREVENTING MATERIAL AND PROCESS FOR PREVENTING ADHESION

(75) Inventors: Yotaro Izumi, Tokyo (JP); Masafumi Kawamura, Tokyo (JP); Koichi Kobayashi, Tokyo (JP)

(73) Assignees: Keio University, Tokyo (JP); Meiji Seika Kaisha, Ltd., Tokyo (JP)

( * ) Notice: Subject to any disclaimer, the term of this patent is extended or adjusted under 35 U.S.C. 154(b) by 824 days.

(21) Appl. No.: 11/666,337

(22) PCT Filed: Nov. 17, 2005

(86) PCT No.: PCT/JP2005/021094
§ 371 (c)(1),
(2), (4) Date: Apr. 26, 2007

(87) PCT Pub. No.: WO2006/054624
PCT Pub. Date: May 26, 2006

(65) Prior Publication Data
US 2008/0118907 A1 May 22, 2008

(30) Foreign Application Priority Data
Nov. 18, 2004 (JP) .................................. 2004-333835

(51) Int. Cl.
*A01N 1/00* (2006.01)
(52) U.S. Cl. ........................................ 435/1.1; 424/423
(58) Field of Classification Search .................... 435/1.1
See application file for complete search history.

(56) References Cited

U.S. PATENT DOCUMENTS

| 5,505,952 | A | 4/1996 | Jiang et al. |
| 5,854,381 | A | 12/1998 | Jürgens et al. |
| 2002/0197296 | A1 | 12/2002 | Gen |
| 2003/0091646 | A1 | 5/2003 | Gen |

FOREIGN PATENT DOCUMENTS

| JP | 3-295561 | 12/1991 |
| JP | 6-322358 | 11/1994 |
| JP | 11-276572 | 10/1999 |
| JP | 2000-237294 | 9/2000 |
| JP | 2003-000695 | 1/2003 |

OTHER PUBLICATIONS

U.S. Appl. No. 12/227,379.*
English translation of JP 6-322358 (corresponds to reference "AM" on Information Disclosure Statement filed Apr. 26, 2007).
English translation of JP 11-276572 (corresponds to reference "AI" on Information Disclosure Statement filed Apr. 26, 2007).

* cited by examiner

*Primary Examiner* — Ruth A Davis
(74) *Attorney, Agent, or Firm* — Wenderoth, Lind & Ponack, L.L.P.

(57) ABSTRACT

An object of the present invention is to provide an adhesion-preventing material which is capable of effectively preventing the surfaces of organs from adhesion, and which can be absorbed in the body with high safety and produced with ease and has high practical utility, as well as to a process for preventing adhesion by using the adhesion-preventing material.

The present invention provides (1) an adhesion-preventing material comprising a crosslinked water absorbent poly-γ-glutamic acid as an effective ingredient; (2) the adhesion-preventing material described above, wherein the crosslinked water absorbent poly-γ-glutamic acid is in the form of powder having a water absorption coefficient in the range of 800-2000; (3) a process for preventing organ from adhesion, comprising a step of bringing the adhesion-preventing material described above into contact with the surface of a local organ; and (4) the process for preventing adhesion described above, wherein the surface of the local organ is in wet state.

9 Claims, 2 Drawing Sheets

ADHESION-PREVENTING MATERIAL AND PROCESS FOR PREVENTING ADHESION

This application is a National Stage Entry of PCT/JP2005/021094, filed Nov. 17, 2005.

BACKGROUND OF THE INVENTION

1. Technical Field

The present invention relates to an adhesion-preventing material and a process for preventing adhesion, in particular to an adhesion-preventing material which is capable of effectively preventing the surfaces of organs from adhesion, and which can be absorbed in the body with high safety and manufactured with ease and has high practical utility, as well as to a process for preventing adhesion by using the adhesion-preventing material.

2. Background Art

Organs are generally in a state which can be freely moved or separated with each other even if the surface of an organ is in proximal contact with that of the other organ. However, adhesion between organs may be caused by inflammation due to operation or some other causes, which brings about deuteropathy such as hypofunctions of local organs. When the adhesion of organs is caused, it is necessary to conduct re-operation, which increases the burden on the patient, and the operation is very difficult to be completed.

Adhesion-preventing materials have been proposed for the purpose of preventing the adhesion of organs.

Adhesion-preventing materials are broadly classified into non-absorbent and absorbent materials.

The non-absorbent materials include silicone sheet, Gore-Tex sheet, organ-adhesion preventing films comprising a hydrogel film of a mixed polymer which comprises polyvinyl alcohol and a prescribed water-soluble polymer (see Patent Reference 1). While these sheets physically isolate a damaged site by affixing the sheet to the site, resulting in no adhesion, they are not absorbed in the body and thus offer a problem that an artificial material remains in the body.

Furthermore, the non-absorbent sheet or film thus affixed itself may cause dysfunction by adhering to organs. In this case, it will be impossible to remove the sheet thus adhered to the organs even by re-operation.

Therefore, it has been attempted to develop absorbent base materials which can be absorbed in the body with high safety.

There have been proposed, as the absorbent base material, gelatin, fibrin glue, hyaluronic acid and salts thereof, cellulose, as well as an adhesion-preventing material comprising poly-γ-glutamate complexes formed by hydrogen bonding of the carboxy anion of the poly-γ-glutamate with chitosan or the like (see Patent Reference 2), a radiation-sterilizable medical material comprising a bioavailable polymer and a multi-functional triazine compound such as triallyl-isocyanurate contained therein(see Patent Reference 3), and the like.

While the absorbent base materials can be repeatedly used in the same site with high safety, only a few of the materials have been recognized effective in animal experiments and thus it is difficult to say that the materials have been spread clinically. Especially, high probability of side effects may be found in such materials comprising animal proteins as the primary ingredient, and a two-ingredient based material such as the adhesion-preventing materials disclosed in Patent References 2 and 3.

Moreover, a biodegradable and highly water-absorbent material composed of a radiation-crosslinked poly-γ-glutamate polymer having a gelation degree of 40-90% has been proposed in Patent Reference 4. Patent Reference 4 focuses on the manufacturing conditions, water absorption properties and biodegradability of the biodegradable and highly water-absorbent material. However, Patent Reference 4 does not disclose the use of the highly water-absorbent material as an adhesion-preventing material.

Patent Reference 1: Japanese Patent No. 2840729,
Patent Reference 2: Japanese Patent Laid-Open Publication No. 276572/1999,
Patent Reference 3: Japanese Patent Laid-Open Publication No. 695/2003,
Patent Reference 4: Japanese Examined Patent Publication No. 72267/1995.

DESCRIPTION OF THE INVENTION

Problem to be Solved by the Invention

An object of the present invention is to provide an adhesion-preventing material which is capable of effectively preventing the surfaces of organs from adhesion, and which can be absorbed in the body with high safety and manufactured with ease and has high practical utility, as well as to a process for preventing adhesion by using the adhesion-preventing material.

Means for Solving Problem

The present inventors has earnestly conducted investigation for the purpose of solving the above problem, and found as the result that a crosslinked water absorbent poly-γ-glutamic acid is useful as an effective ingredient of an adhesion-preventing material. Specifically, it has been found that the crosslinked water absorbent poly-γ-glutamic acid has a viscosity not to be easily swept away by the surrounding water, so that not only the surface of local organs, for example, post-operative local organs, is effectively prevented from adhesion, but also no side effect is induced. It has also been found that bleeding, which is of a small amount, can be stopped with high possibility.

The present invention is based on such findings as described above.

The present invention according to claim 1 is an adhesion-preventing material comprising a crosslinked water absorbent poly-γ-glutamic acid as an effective ingredient.

The present invention according to claim 2 is the adhesion-preventing material according to claim 1, wherein the crosslinked water absorbent poly-γ-glutamic acid is in the form of powder having a water absorption coefficient in the range of 800-2000.

The present invention according to claim 3 is a process for preventing organ from adhesion, comprising a step of: bringing the adhesion-preventing material according to claim 1 or 2 into contact with the surface of a local organ.

The present invention according to claim 4 is the process according to claim 3, wherein the surface of the local organ is in wet state.

Effects of the Invention

According to the present invention, an adhesion-preventing material which is capable of effectively preventing the surfaces of organs from adhesion, and which can be absorbed in the body with high safety (for example, without side effects) and produced with ease and has high practical utility, as well as to a process for preventing adhesion by using the adhesion-preventing material are provided.

BEST MODE FOR CARRYING OUT THE INVENTION

Figure 1:
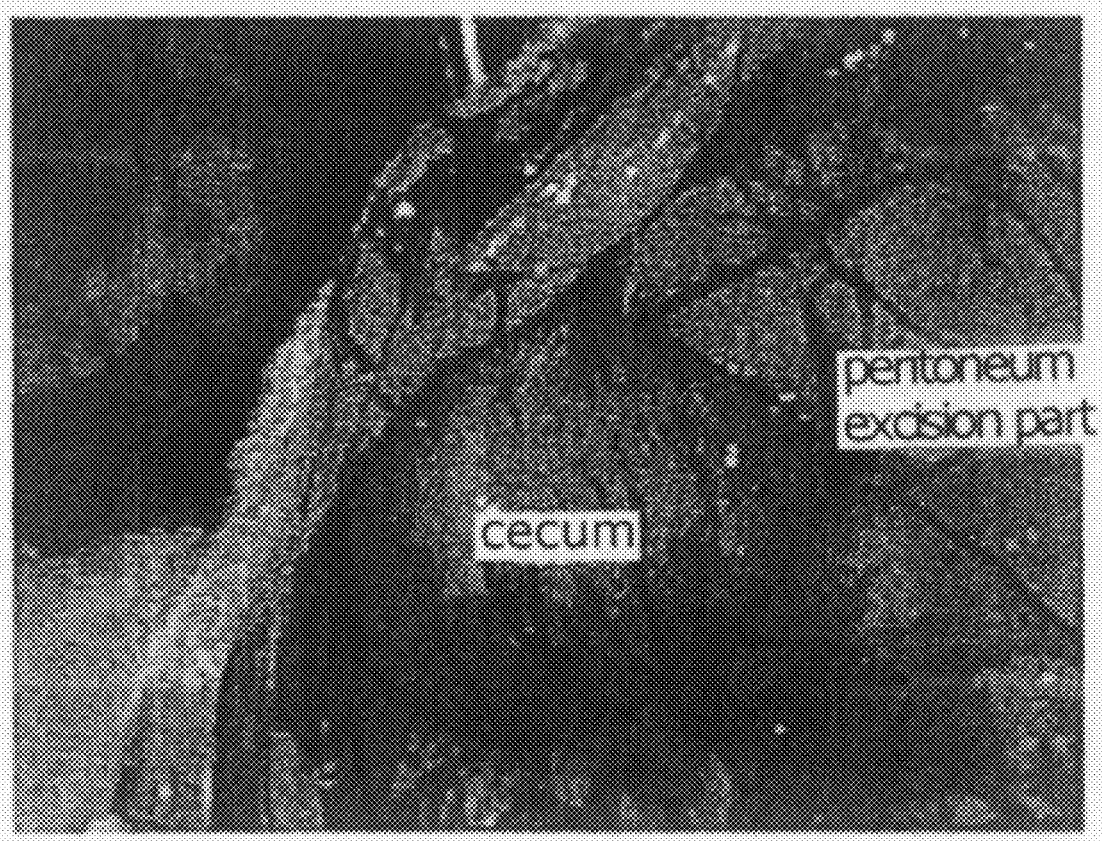
FIG. 1 shows the state of adhesion in the non-treated group in Example 1.

An adhesion-preventing material according to the present invention comprises a crosslinked water absorbent poly-γ-glutamic acid as an effective ingredient.

As used herein, the term "crosslinked water absorbent poly-γ-glutamic acid" means the hydrophilic polymer molecule, poly-γ-glutamic acid, which takes a matrix structure by crosslinking formation and has the capacity of maintaining water in the structure. In other words, it is a so-called hydrogel wherein water can be retained within the three-dimensional network constructed by the crosslinking of the poly-γ-glutamic acid. The water absorption property of the crosslinked water absorbent poly-γ-glutamic acid is so favorable as to retain water in several thousand times of its weight.

The crosslinking of the poly-γ-glutamic acid means the crosslinking of a poly-γ-glutamic acid with the other one directly or through a crosslinking agent.

As used herein, the term "poly-γ-glutamic acid" means a polymer of glutamic acid, in which D- and L-glutamic acids are linked in the γ-position to form an acidic water soluble polymer having a molecular weight in the range of 200,000-2,000,000. The poly-γ-glutamic acid includes a salt thereof with alkali metal, alkaline earth metal, and the like. Also, the poly-γ-glutamic acid includes those composed only of the D-glutamic acid or those composed only of the L-glutamic acid. The poly-γ-glutamic acid is a main ingredient of a viscous substance in fermented soybeans and commonly used for food, confirming safety for organisms. In addition, it is biodegraded in soil and thus of no risk of environmental pollution. Therefore, it has been recognized useful for moisture retention of the skin and currently used for cosmetics.

The poly-γ-glutamic acid may be prepared by any method without any limitation, and includes those produced by *bacillus* microorganisms such as *Bacillus subtilis, Bacillus anthracis, Bacillus megaterium, Bacillus natto*, and the like (see Biosci. Biotech., 56, 1031-1035 (1992); Japanese Patent Laid-Open Publication No. 174397/1989) and those obtained by chemical synthesis or the like. Also, the poly-γ-glutamic acid obtained may be purified by any method without any limitation, and the purification can be conducted, for example, according to the method described in Japanese Patent Laid-Open Publication No. 316286/1995.

The crosslinked water absorbent poly-γ-glutamic acid may be prepared by crosslinking the poly-γ-glutamic acid under the conditions which can be appropriately selected dependent on the desired molecular weight and water absorption coefficient. The crosslinking method includes the methods of polymerizing the poly-γ-glutamic acid by the γ-ray radiation or by the chemical bonding with a crosslinking agent, or the like.

In the case of the polymerization by γ-ray radiation, it may be carried out according to the method described in Japanese Examined Patent Publication No. 72267/1995. That is to say, the poly-γ-glutamic acid as the raw material is dissolved in water or a mixed solvent of water and a water-soluble solvent so that the concentration of the poly-γ-glutamic acid is in the range of 1.5-6% by weight, and the radiation is applied to the resulting solution, after which the crosslinked product can be separated. The radiation dose in this case can be appropriately set generally in the range of 1.0-50 Mrad (10-500 kGy), preferably in the range of 1.5-40 Mrad (15-400 kGy), and more preferably in the range of 2-30 Mrad (20-300 kGy).

Moreover, in the case of the polymerization by chemical synthesis with a crosslinking agent, it can be carried out according to the methods described in Japanese Patent Laid-Open Publication No. 343339/1999 or 128899/2002. That is to say, the poly-γ-glutamic acid or a salt thereof as the raw material can be directly reacted with a compound (crosslinking agent) having two or more functional groups which can be reacted with the carboxyl group at the side chain of the poly-γ-glutamic acid, or reacted with a crosslinking agent in the presence of a condensation agent to give a water absorbent crosslinked product.

The crosslinked water absorbent poly-γ-glutamic acid used for the present invention has a high water absorption capacity. The water absorption capacity can be represented by the water absorption coefficient as an index.

The water absorption coefficient is a value (g/g) obtained by dividing the weight of absorbed water (g) by the weight of a sample (i.e. the weight of the crosslinked water absorbent poly-γ-glutamic acid) (g) as in Reference Example 1 described later. The water absorption coefficient in the range of 500-2500 g/g, preferably in the range of 800-2000 g/g, more preferably in the range of 900-1200 g/g is preferred, since the crosslinked water absorbent poly-γ-glutamic acid can be applied even to the surface of the local organ in wet state.

The crosslinked water absorbent poly-γ-glutamic acid described above has the property of roping gel which is formed by mixing lightly with a finger the crosslinked product sprayed for example on a Petri dish with a small amount of distilled water.

The adhesion-preventing material of the present invention, which comprises the crosslinked water absorbent poly-γ-glutamic acid as the effective ingredient, can comprise the other ingredients such as a stabilizing agent, an anti-oxidant, a coloring agent, if necessary, without particular limit for the content of the crosslinked water absorbent poly-γ-glutamic acid.

Also, the adhesion-preventing material of the present invention is not particularly limited for the form thereof and includes, for example, in the form of powder, solution, sol, gel (jelly), sheet, and the like, which is preferably in the form of solid to a certain extent, most preferably in the form of powder with regard to its operational property.

In this connection, the adhesion-preventing material of the present invention can be also used as a mixture with the other ingredients effective for the prevention of adhesion, such as fibrin glue or sodium hyaluronate. It can be used in combination by embedding it in the surface of the other adhesion-preventing material sheet as well.

The adhesion-preventing material of the present invention is highly safe in that it prevents effectively the adhesion of the surfaces of local organs, as well as promotes the healing of an injury at the surface of the local organs and is absorbed in the body without side effects. Moreover, it may stop bleeding, which is of a small amount, with high possibility, and such hemostatic effect has not been found in the conventional adhesion-preventing material.

Therefore, the adhesion-preventing material of the present invention can be used for preventing the adhesion of surfaces of the post-operative local organs, and thus the present invention also provides a process for preventing adhesion of such organs.

In other words, the process for preventing adhesion of organs according to the present invention comprises bringing the adhesion-preventing material into contact with the surfaces of local organs. In this connection, the term "contact" means herein the contact by coating or spraying the adhesion-preventing material on the surface of the local organ.

The term "the surface of the local organ" means herein all or a part of the surface of an organ in which inflammation is caused by operations such as surgical operation or some etiology and thus it is required to prevent the adhesion. The site or type of the organs is preferably, but not limited to, the organs other than the surface of the body (skin) of mammals including human being, experimental animals such as mice, rats, rabbits, and the like, and domestic animals. The organs include, for example, digestive organs such as stomach, small intestine and large intestine, genital organs such as uterus and ovary, respiratory organs such as heart and lung, locomotoria such as muscle, bone, and ligament, sense organs such as eye, and the like.

The type of surgery of organs is not limited. Also, the surface of the local organ may be a direct target of the surgery, or a damaged part which is not the direct target of the surgery but damaged as the result of the surgery.

The surface of the local organ is not also limited to particular states. The adhesion-preventing material of the present invention is water soluble and thus can be applied to the surface without being carried away even in wet state.

In the process for preventing adhesion of organs according to the present invention, the form of the adhesion-preventing material and the percentage of the effective ingredient in the process for bringing the adhesion-preventing material into contact with the surface of the local organ can be appropriately determined depending on the kinds of organs and the states of wound parts. As the adhesion-preventing material according to the present invention exhibits no side effects and is highly safe, the amount of the adhesion-preventing material contacted with the surface of the local organs can be set in a range of covering the surface.

In the case of the adhesion-preventing material in the gel form, the effect of the method for preventing adhesion of organs of the present invention is judged by visually observing the existence of adhesion after one week of coating the surface of local organs (for example, in wet state) with the adhesion-preventing material. In general, the adhesion-preventing material becomes invisible to the naked eye within about 48 hours after coating with it. In this connection, if the adhesion is not caused at this point of time, it can be judged that the adhesion is effectively prevented, although it depends on the types of the organs or the states of the surface of the organs.

EXAMPLES

The present invention is described more specifically with reference to the following examples.

Referential Example 1

Water Absorption

First, the water absorption coefficient of the crosslinked water absorbent poly-γ-glutamic acid (referred to hereinafter as PGA-XL) was determined.

Four PGA-XLs were provided as samples: PGA-XL (0203·15K), PGA-XL (0203·20K) and PGA-XL (0203·25K) which were prepared by crosslinking poly-γ-glutamic acid (trade name: Meiji Bio PGA, Meiji Seika Kaisha, Ltd.) using γ-ray irradiation with a dose of 15 kGy, 20 kGy and 25 kGy respectively; and powdery PGA-XL (020531M, trade name: Meiji Bio PGA-XL, Meiji Seika Kaisha, Ltd.) crosslinked by γ-ray irradiation with a dose of 20 kGy.

About 0.1 g of each sample was precisely weighed and placed in a one-liter beaker, and 1 liter of deionized water was added thereto. The top of the beaker was covered with aluminum foil and left standing overnight in a low temperature chamber at 5° C. in order to avoid the influence of temperature.

A two-liter beaker was covered with four layers of gauzes (Japanese Pharmacopoeia; type I), on which the content of the one-liter beaker was poured. After pouring all of the content, gel, if remained in the one-liter beaker, was scraped off with a spatula and placed on the gauzes. After being left standing for 1 hour, the gel remained on the gauzes were placed in a 500 ml beaker of which tare weight had been preliminarily measured. The gel sticked to the gauzes was also scraped off with a spatula to place into the 500 ml beaker. The tare weight of the 500 ml beaker was subtracted from the total weight of the beaker at this time to obtain the value as the water absorption. In addition, the water absorption coefficient was calculated from the following equation. The types of the samples, the weights of the samples, the doses of the γ-ray, and the water absorption coefficients are listed in Table 1.

Water absorption coefficient (g/g)=Water absorption (g)/Sample weights (g)

TABLE 1

| Sample | Manufacturing No. | Sample weight | Irradiation Dose | Water absorption coefficient |
|---|---|---|---|---|
| PGA-XL | 0203.15K | 3 g | 15 kGy | 807 |
| PGA-XL | 0203.20K | 3 g | 20 kGy | 2112 |
| PGA-XL | 0203.25K | 3 g | 25 kGy | 1260 |
| PGA-XL | 020531M | 3 g | 20 kGy | 1090 |

It has been revealed from the results of Table 1 that a variety of the crosslinked water absorbent poly-γ-glutamic acid having different doses and water absorption coefficients can be provided.

Example 1

Adhesion Preventing Effect

Subsequently, the adhesion preventing effects were measured for the crosslinked water absorbent poly-γ-glutamic acid (PGA-XL; the present invention), and the controls a non-crosslinked poly-γ-glutamic acid (non-crosslinked PGA) and sodium hyaluronate.

As the crosslinked water absorbent poly-γ-glutamic acid (PGA-XL; the present invention), 020531M among PGA-XLs in Referential Example 1 was used. Poly-γ-glutamic acid used as the raw material for preparation of PGA-XL in Referential Example 1 was used directly as the non-crosslinked poly-γ-glutamic acid (non-crosslinked PGA). As the sodium hyaluronate, the one available from Meiji Seika Kaisha, Ltd. (molecular weight: 1,200,000) was used.

Donryu rats (male, 5-7 weeks old) were divided into four groups so that each group was composed of 6-9 rats. For each group, the rats were subjected to laparotomy under general anesthetization (abdominal midline incision) to excise the abdominal wall right above the ileocecum of large intestine in a size of about 1×2 cm. The ileocecum was then moved out of the abdominal cavity, and the surface of the serous membrane of the ileocecum was rubbed with gauze until the appearance of small bleeding spots. Furthermore, the surface was heated with a drier for about 20 seconds and then dried in the room air for about 10 minutes.

As for the crosslinked water absorbent poly-γ-glutamic acid (PGA-XL; the present invention) and the non-crosslinked poly-γ-glutamic acid, 0.2 g thereof was coated on the part of the serous membrane rubbed with gauze and the part where peritoneum and abdominal wall had been excised. As for the hyaluronic acid, a 0.4% aqueous solution thereof was prepared, and an about 2 ml portion of the solution was sprayed around the affected part so as to be spread over the abdominal cavity. Then, the damaged part and the part where the peritoneum and the abdominal wall had been excised were contacted with each other and the abdomen was closed.

After about a week, the degree of adhesion in each group was observed by laparotomy, and the adhesion was evaluated on the basis of grades consisting of "none" where no adhesion was observed, "low" where blunt dissection can be done, "moderate" where sharp dissection can be done, and "high" where adhesion was observed in such an extent that the organs are damaged by dissection.

Figure 2:
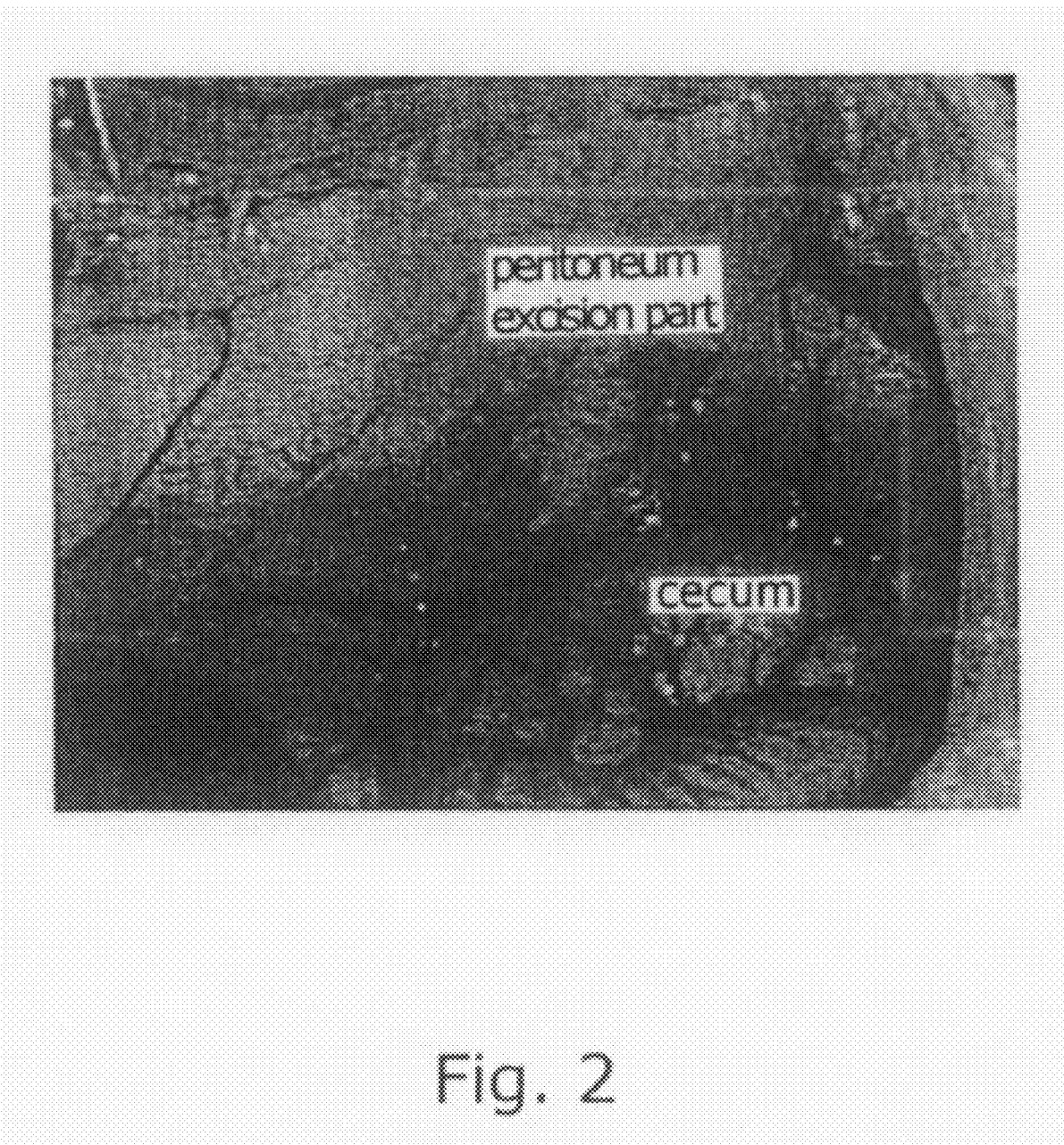
FIG. 2 shows the state of the prevention of adhesion in the group treated with the crosslinked water absorbent poly-γ-glutamic acid in Example 1.

The results of the dissection test are shown in Table 2, where the results of the non-treated group are also shown. In addition, the state of the non-treated group upon laparotomy after a week is shown in FIG. 1, and the state of the crosslinked water absorbent poly-γ-glutamic acid group is shown in FIG. 2.

TABLE 2

| Sample | Extent of adhesion | | | | Total |
|---|---|---|---|---|---|
| | None | Low | Moderate | High | |
| Sodium hyaluronate | 0 | 1 | 2 | 3 | 6 |
| PGA-XL (the present invention) | 9 | 0 | 0 | 0 | 9 |
| Non-crosslinked PGA | 3 | 4 | 0 | 0 | 7 |
| Non-treated group | 0 | 0 | 0 | 6 | 6 |

As shown in Table 2, high degree of adhesion was observed in all of the individuals in the non-treated group (see FIG. 1), and it was observed also in the half of the individuals in the sodium hyaluronate group. Moreover, low degree of adhesion was observed in four rats in the non-crosslinked PGA group. In contrast to these observations, adhesion was not observed in any individual animals in the crosslinked water absorbent poly-γ-glutamic acid (PGA-XL; the present invention) group (see FIG. 2). No adhesion was observed in other parts than the treated part in the abdominal cavity.

Furthermore, when the crosslinked water absorbent poly-γ-glutamic acid (PGA-XL; the present invention) was coated, it was confirmed that the existence of the coat became ambiguous at the site of coating at the time of 48 hours from the treatment and thus the coat was absorbed in the body.

Example 2

Adhesion Preventing Effect; Comparison With the Conventional Products

The adhesion preventing effects of the crosslinked water absorbent poly-γ-glutamic acid (PGA-XL; the present invention) and the non-crosslinked poly-γ-glutamic acid, sodium hyaluronate, Seprafilm and Interceed as the controls were measured as follows. The adhesion preventing effect of the non-treated group was also measured.

As the crosslinked water absorbent poly-γ-glutamic acid (PGA-XL; the present invention), 020531M among the PGA-XLs in Referential Example 1 was used. Poly-γ-glutamic acid used as the raw material for preparation of PGA-XL in Referential Example 1 was used directly as the non-crosslinked poly-γ-glutamic acid (non-crosslinked PGA). As the sodium hyaluronate, the one available from Meiji Seika Kaisha, Ltd. (molecular weight: 1,200,000) was used. As the Seprafilm, the one available from Genzyme, USA was used, and as the Interceed, the one available from Ethicon, USA was used.

Donryu rats (male, 5-7 weeks old) were divided into six groups so that each group was composed of 10-16 rats. For each group, the rats were subjected to laparotomy under general anesthetization (abdominal midline incision) to excise the abdominal wall right above the ileocecum of large intestine in a size of about 1×2 cm. The ileocecum was then moved out of the abdominal cavity, and the surface of the serous membrane of the ileocecum was rubbed with gauze until the appearance of small bleeding spots. Furthermore, the surface was heated with a drier for about 20 seconds and then dried in the room air for about 10 minutes.

As for the crosslinked water absorbent poly-γ-glutamic acid (PGA-XL; the present invention) and the non-crosslinked poly-γ-glutamic acid, 0.2 g of the sample was coated on the part of the serous membrane rubbed with gauze and the part where peritoneum and abdominal wall had been excised. As for the sodium hyaluronate, a 0.4% aqueous solution thereof was prepared, and an about 2 ml portion of the solution was sprayed around the affected part so as to be spread over the abdominal cavity. The Seprafilm and the Interceed were applied after cut into a size sufficient to cover the affected part. Then, the damaged part and the part where the peritoneum and the abdominal wall had been excised were contacted with each other and the abdomen was closed.

After about a week, the degree of adhesion in each group was observed by laparotomy. The degree of adhesion was scored and evaluated for comparison as follows. The results are listed in Table 3.

Score: 0, no adhesion;
1, low adhesion where blunt dissection can be done;
2, 50% or less of sharp dissection;
3, 50% or more of sharp dissection;
4, cecal serous membrane was damaged upon dissection;
5, the all layers of cecum were damaged upon dissection.

TABLE 3

| Score | Group | | | | | |
|---|---|---|---|---|---|---|
| | Non-treated | Non-crosslinked PGA | PGA-XL (the present invention) | Sodium hyaluronate | Seprafilm | Interceed |
| 0 | 0 | 9 | 15 | 0 | 0 | 0 |
| 1 | 1 | 5 | 1 | 0 | 3 | 1 |
| 2 | 0 | 2 | 0 | 5 | 8 | 5 |
| 3 | 6 | 0 | 0 | 3 | 1 | 3 |

TABLE 3-continued

| | Group | | | | | |
|---|---|---|---|---|---|---|
| Score | Non-treated | Non-crosslinked PGA | PGA-XL (the present invention) | Sodium hyaluronate | Seprafilm | Interceed |
| 4 | 3 | 0 | 0 | 4 | 0 | 1 |
| 5 | 2 | 0 | 0 | 0 | 0 | 0 |
| Mean | 3.4 ± 1.1 | 0.6 ± 0.7* | 0.1 ± 0.3* | 3.0 ± 0.9 | 1.8 ± 0.6** | 2.4 ± 0.8*** |

*$p < 0.05$ (against all groups other than the non-treated group);
**$p < 0.05$ (against the non-treated group and sodium hyaluronate);
***$p < 0.05$ (against non-treated group).

As shown in Table 3, the adhesion of low to moderate degree was observed also in the Seprafilm and Interceed groups. The adhesion of low degree was observed also in the non-crosslinked poly-γ-glutamic acid (non-crosslinked PGA) group.

In contrast, only one case of adhesion of low degree was observed in the crosslinked water absorbent poly-γ-glutamic acid (PGA-XL; the present invention) group.

Preparation Example

Process for Preparing a Crosslinked Water Absorbent Poly-γ-glutamic Acid

The conditions of preparing the crosslinked water absorbent poly-γ-glutamic acid (referred to hereinafter as PGA-XL) were studied depending on the doses of γ-ray. A non-crosslinked poly-γ-glutamic acid (non-crosslinked PGA; M.W.: 320,000; manufacturing no.: 90630) was used as the sample. In this connection, the molecular weight was measured by the generally used gel permeation chromatography-light scattering (GPC) method using pullulan as the standard.

The 3% and 5% solutions of the sample were subjected to the γ-ray irradiation. Either of the sample solutions was dissolved in a 4% aqueous solution of sodium hydrogen carbonate, and, if necessary, the solution was adjusted to pH 7.0 with a 4N aqueous solution of sodium hydroxide.

Each of the sample solutions in glass vials was irradiated with γ-ray under each irradiation condition of the test sections (1-14) in Table 4 at Komazawa Branch of Tokyo Metropolitan Industrial Technology Research Institute. Then, the sample solutions were lyophilized at a reduced pressure of 0.08 Torr for 72 hours.

In addition, the water absorption coefficient of PGA-XL obtained was determined by the same method as in Reference Example 1 (water absorption).

TABLE 4

| Test section | Dose (kGy) (18 hours) | Concentration of non-crosslinked PGA (%) | Amount of sample (ml) |
|---|---|---|---|
| 1 | 5.5 | 3 | 25 |
| 2 | | 5 | 25 |
| 3 | 9.5 | 3 | 25 |
| 4 | | 5 | 25 |
| 5 | | 3 | 50 |
| 6 | | 5 | 50 |
| 7 | 20 | 3 | 25 |
| 8 | | 5 | 25 |
| 9 | | 3 | 50 |
| 10 | | 5 | 50 |
| 11 | 26.1 | 3 | 25 |
| 12 | | 5 | 25 |
| 13 | 34.2 | 3 | 25 |
| 14 | | 5 | 25 |

When the production was completed, the sample solutions in the test sections 7-14 were solidified to form crosslinked products. In addition, the water absorption coefficient was measured for the crosslinked products in six test sections among those products thus obtained, and the values shown in Table 5 were obtained. Moreover, when adhesion preventing test was carried out with Donryu rats for the test sections 7 and 10, adhesion between organs was not observed, and it was confirmed that the samples in these test sections are effective for preventing the adhesion.

TABLE 5

| Test section | Concentration of non-crosslinked PGA (%) | Dose (kGy) | Water absorption coefficient |
|---|---|---|---|
| 7 | 3 | 20 | 2497 |
| 11 | | 26.1 | 2196 |
| 13 | | 34.2 | 1030 |
| 8 | 5 | 20 | 580 |
| 12 | | 26.1 | 2348 |
| 14 | | 34.2 | 1522 |

INDUSTRIAL APPLICABILITY

According to the present invention, an adhesion-preventing material which is capable of effectively preventing the surfaces of organs from adhesion, and which can be absorbed in the body with high safety (for example, without side effects) and produced with ease and has high practical utility, as well as to a process for preventing adhesion by using the adhesion-preventing material are provided.

The invention claimed is:

1. An adhesion-preventing material comprising a crosslinked water absorbent poly-γ-glutamic acid as an effective ingredient, wherein the crosslinked water absorbent poly-γ-glutamic acid is prepared by crosslinking of a poly-γ-glutamic acid with another poly-γ-glutamic acid directly.

2. The adhesion-preventing material according to claim 1, wherein the crosslinked water absorbent poly-γ-glutamic acid is in the form of powder having a water absorption coefficient in the range of 800-2000.

3. A process for preventing organ adhesion, comprising a step of:

bringing a crosslinked water absorbent poly-γ-glutamic acid as an effective ingredient into contact with a surface of a local organ, wherein the crosslinked water absorbent poly-γ-glutamic acid is prepared by crosslinking of a poly-γ-glutamic acid with another poly-γ-glutamic acid directly.

4. The process according to claim 3, wherein the surface of the local organ is in a wet state.

5. A process for preventing organ adhesion, comprising a step of:

bringing a crosslinked water absorbent poly-γ-glutamic acid as an effective ingredient into contact with a surface of a local organ wherein the crosslinked water absorbent poly-γ-glutamic acid is in the form of powder having a water absorption coefficient in the range of 800-2000, wherein the crosslinked water absorbent poly-γ-glutamic acid is prepared by crosslinking of a poly-γ-glutamic acid with another poly-γ-glutamic acid directly.

6. The process according to claim 5, wherein the surface of the local organ is in a wet state.

7. The adhesion-preventing material according to claim 1, wherein the crosslinked water absorbent poly-γ-glutamic acid is prepared by crosslinking the poly-γ-glutamic acid by gamma-ray radiation.

8. The process according to claim 3, wherein the crosslinked water absorbent poly-γ-glutamic acid is prepared by crosslinking the poly-γ-glutamic acid by gamma-ray radiation.

9. The process according to claim 5, wherein the crosslinked water absorbent poly-γ-glutamic acid is prepared by crosslinking the poly-γ-glutamic acid by gamma-ray radiation.

* * * * *